(12) United States Patent
Hillman et al.

(10) Patent No.: US 8,619,237 B2
(45) Date of Patent: Dec. 31, 2013

(54) LASER-SCANNING INTERSECTING PLANE TOMOGRAPHY SUCH AS FOR HIGH SPEED VOLUMETRIC OPTICAL IMAGING

(75) Inventors: Elizabeth Marjorie Clare Hillman, New York, NY (US); Matthew B. Bouchard, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 188 days.

(21) Appl. No.: 12/961,074

(22) Filed: Dec. 6, 2010

(65) Prior Publication Data

US 2012/0140240 A1   Jun. 7, 2012

Related U.S. Application Data

(60) Provisional application No. 61/283,523, filed on Dec. 4, 2009, provisional application No. 61/342,359, filed on Apr. 13, 2010.

(51) Int. Cl.
*G01C 3/08* (2006.01)
*G01C 11/12* (2006.01)

(52) U.S. Cl.
USPC .............................................. 356/2; 356/5.01

(58) Field of Classification Search
USPC ................. 356/2, 4.01, 5.01, 5.13, 600–636; 382/154, 106; 250/559.45, 559.39, 250/559.18, 559.46
See application file for complete search history.

(56) References Cited

U.S. PATENT DOCUMENTS 4,965,441 A   10/1990   Picard
5,006,721 A  *  4/1991   Cameron et al. ......... 250/559.16

(Continued)

FOREIGN PATENT DOCUMENTS

WO   WO-2009/005748 A1   1/2009

OTHER PUBLICATIONS

"Applications in Confocal Microscopy: Fluorescence Lifetime Imaging Microscopy (FLIM)", © 2004-2009 Olympus Corporation, [online]. [retrieved Dec. 9, 2010]. Retrieved from the Internet: <URL: http://www.olympusfluoview.com/applications/flimintro.html>, 3 pgs.

(Continued)

*Primary Examiner* — Sang Nguyen
(74) *Attorney, Agent, or Firm* — Schwegman, Lundberg & Woessner P.A.

(57) ABSTRACT

Laser-Scanning Intersecting Plane Tomography (L-SIPT) can provide a non-contact imaging geometry that can allow high speed volumetric scanning, such as of non-scattering to moderately scattering tissues. The L-SIPT imaging apparatus can include a first lens, located and configured to receive from a sample light received from different depths of the sample. A first light redirector can be located and configured to receive via the first lens and to redirect light received from the different depths of the sample to provide redirected light to a light detector capable of detecting individual measurements of light at different locations along a first direction. A second light redirector can be located and configured to redirect light received from a light source to provide redirected light to the sample, wherein the second light redirector is in a specified spatial relationship to the first light redirector, and wherein the first and second light redirectors are configured to be adjusted during a scan of the sample so as to provide the specified spatial relationship during the scan.

24 Claims, 5 Drawing Sheets

(56) References Cited

U.S. PATENT DOCUMENTS

| | | | |
|---|---|---|---|
| 5,305,092 A * | 4/1994 | Mimura et al. | 356/609 |
| 5,453,851 A * | 9/1995 | Faulhaber | 358/481 |
| 5,489,985 A * | 2/1996 | Mochida et al. | 356/398 |
| 5,493,388 A * | 2/1996 | Adachi | 356/5.01 |
| 5,510,889 A * | 4/1996 | Herr | 356/5.1 |
| 5,627,308 A * | 5/1997 | Dahneke | 73/28.01 |
| 5,719,399 A | 2/1998 | Alfano et al. | |
| 5,790,243 A * | 8/1998 | Herr | 356/5.1 |
| 5,914,495 A * | 6/1999 | Ishizuka et al. | 250/559.45 |
| 6,115,114 A * | 9/2000 | Berg et al. | 356/5.13 |
| 6,208,749 B1 | 3/2001 | Gutkowicz-Krusin et al. | |
| 6,341,036 B1 | 1/2002 | Tearney et al. | |
| 6,399,936 B1 | 6/2002 | Hang et al. | |
| 6,480,287 B2 * | 11/2002 | Lee et al. | 356/607 |
| 6,615,063 B1 | 9/2003 | Ntziachristos et al. | |
| 6,674,893 B1 * | 1/2004 | Abe et al. | 382/154 |
| 6,775,404 B1 | 8/2004 | Pagoulatos et al. | |
| 6,809,815 B2 | 10/2004 | Knebel | |
| 6,825,930 B2 | 11/2004 | Cronin et al. | |
| 7,107,116 B2 | 9/2006 | Geng | |
| 7,147,153 B2 | 12/2006 | Rowe et al. | |
| 7,231,243 B2 | 6/2007 | Tearney et al. | |
| 2004/0054248 A1 | 3/2004 | Kimchy et al. | |
| 2004/0054270 A1 | 3/2004 | Pewzner et al. | |
| 2005/0171439 A1 | 8/2005 | Maschke et al. | |
| 2007/0035721 A1 * | 2/2007 | Toshikiyo et al. | 356/73.1 |
| 2008/0225299 A1 * | 9/2008 | Ono | 356/447 |
| 2009/0296207 A1 * | 12/2009 | Goelles et al. | 359/385 |
| 2010/0168586 A1 | 7/2010 | Hillman et al. | |

OTHER PUBLICATIONS

"DermLite® Pro DP-R: The Ultimate in Handheld Dermoscopy", © 2008 3Gen, LLC. [online]. [retrieved Aug. 29, 2008]. Retrieved from the Internet: <URL: http://www.dermlite.com/pro.html>, (2008), 1 pg.

"International Application Serial No. PCT/US2008/008081, International Search Report and Written Opinion mailed Oct. 1, 2008", 11 pgs.

"Mohs Surgery with the VivaCell® 2500", © Copyright Lucid, Inc., [online]. [retrieved Aug. 29, 2008]: Retrieved: <URL: http://www.lucid-tech.com/medical-imagers/vivacell.asp>, (2008), 2 pgs.

"Siametics™ Skin measurement, In vivo, In seconds", © Copyright Astron Clinica 2007, [online]. Retrieved from the Internet: <URL: http://www.astronclinica.com/products/siametrics.htm>, (2007),4 pgs.

"The MelaFind® System", [online]. [retrieved Aug. 29, 2008]. Retrieved from the Internet: <URL: http://www.eo-sciences.com/technology1.html>, (2008), 1 pg.

Barton, J. K., "Optical coherence tomography", in AccessScience@McGraw-Hill, © 2007 The McGraw-Hill Companies. [online]. [retrieved Aug. 29, 2008]. Retrieved from the Internet: <URL: http://www.accessscience.com, DOI 10.1036/ 1097-8542.757714, (2008), 5 pgs.

Bouchard, M. B., et al., "Laser-Scanning Intersecting Plane Tomography. (L-SIPT) for high speed 3D optical imaging and microscopy". In: OSA Biomedical Topical Meetings, OSA Technical Digest, Optical Society of America, (Apr. 11-14, 2010, Miami, FL), (2010), 3 pgs.

Corlu, A., et al., "Diffuse optical tomography with spectral constraints and wavelength optimization", Applied Optics, 44(11), (Apr. 10, 2005), 2082-2093.

Corlu, A., et al., "Uniqueness and wavelength optimization in continuous-wave multispectral diffuse optical tomography", Optics Letters, 28(23), (Dec. 1, 2003), 2339-2341.

Dunsby, C, "Optically sectioned imaging by oblique plane microscopy", Optics Express, 16(25), (2008), 11 pgs.

Dwyer, P. J., et al., "Confocal Reflectance Theta Line Scanning Microscope for Imaging Human Skin In Vivo", Optics Letters, 31(7), (2006), 942-944.

Dwyer, P. J., et al., "Confocal theta line-scanning microscope for imaging human tissues", Applied Optics, 46(10), (2007), 1843-1851.

Dyba, M., et al., "STED-Microscopy . . . Overcomes the diffraction limit in a fundamental way", [online]. [retrieved Dec. 9, 2010]. Retrieved from the Internet: <URL: http://www.mpibpc.mpg.de/groups/hell/STED.htm>, (2010), 3 pgs.

Fahrbach, F. 0., et al., "Microscopy With Self-Reconstructing Beams", Nature Photonics, 4, (2010), 780-785.

Hillman, E. M., et al.,"Depth-resolved optical imaging and microscopy of vascular compartment dynamics during somatosensory stimulation.", Neuroimage, 35(1), (Mar. 2007), 89-104.

Hillman, E. M., et al., "Supplemental Material for: Depth-resolved Optical Imaging and Microscopy of Vascular Compartment Dynamics During Somatosensory Stimulation", [online]. Retrieved from the Internet: http://www.nmr.mgh.harvard.edu/PMI/PDF/2007/Hillman_NI_2007_supp.pdf, Neuroimage. Mar. 2007;35(1):89-104, (2007), 1-11.

Hillman, E,, "Experimental and theoretical investigations of near infrared tomographic imaging methods and clinical applications.", Thesis submitted for the degree of Doctor of Philosophy (Ph.D.) at the University of London, (Feb. 2002), 1-356.

Huisken, J., et al., "Selective plane illumination microscopy techniques in developmental biology", Development, 136, (2009), 1163-1975.

Li, A., et al., "Optimal linear inverse solution with multiple priors in diffuse optical tomography", Applied Optics, 44(10), (Apr. 1, 2005), 1948-1956.

Stoecker, William, "Automatic Detection of Critical Dermoscopy Features for Melanoma Diagnosis—Grant No. 2R44CA101639-02A2", [online]. [retrieved Aug. 29, 2008]. Retrieved from the Internet: <URL: http://crisp.cit.nih.gov/crisp/CRISP_LIB.getdoc?textkey= 7163231&p_grant_num=2R44CA101639-02A2&p_query=(melanoma+%26+detection)&ticket=67102869&p_audit_session_id=334829146&p_audit_score=39&p_audit_numfound=3&p_keywords=melanoma+detection, CRISP (Computer Retrieval of Information on Scientific Projects) Database, (2006), 2 pgs.

Timmins, G., "Molecular imaging of melanoma by EPR", CRISP (Computer Retrieval of Information on. Scientific Projects) Database, [online]. Retrieved from the Internet: <URL: http://crisp.cit.nih.gov/crisp/CRISP_LIB.getdoc?textkey=7048244&p_grant_num=1R21CA113687-01A1&p_query=(melanoma+%26+detection)&ticket=67102869&p_audit_session_id=334829146&p_audit_score=8&p_audit_numfound=134&p_keywords=melanoma+detection, (2006), 2 pgs.

"U.S. Appl. No. 12/655,325 , Response filed Aug. 23, 2013 to Non Final Office Action mailed Nov. 29, 2012", 17 pgs.

"U.S. Appl. No. 12/655,325, Non Final Office Action mailed Nov. 29, 2012", 10 pgs.

* cited by examiner

LASER-SCANNING INTERSECTING PLANE TOMOGRAPHY SUCH AS FOR HIGH SPEED VOLUMETRIC OPTICAL IMAGING

CLAIM OF PRIORITY

This patent application claims the benefit of priority, under 35 U.S.C. Section 119(e), to Bouchard et al. U.S. Provisional Patent Application Ser. No. 61/283,523, entitled "LASER-SCANNING INTERSECTING PLANE TOMOGRAPHY (L-SIPT) FOR HIGH SPEED 3D OPTICAL IMAGING AND MICROSCOPY," filed on Dec. 4, 2009, which is hereby incorporated by reference herein in its entirety.

This patent application also claims the benefit of priority, under 35 U.S.C. Section 119(e), to Hillman et al. U.S. Provisional Patent Application Ser. No. 61/342,359, entitled "LASER-SCANNING INTERSECTING PLANE TOMOGRAPHY, A NEW TECHNIQUE FOR HIGH SPEED VOLUMETRIC OPTICAL IMAGING," filed on Apr. 13, 2010, which is hereby incorporated by reference herein in its entirety.

CROSS-REFERENCE TO RELATED PATENT DOCUMENTS

This patent application is also related to Hillman et al. U.S. patent application Ser. No. 12/655,325, entitled OPTICAL IMAGING OR SPECTROSCOPY SYSTEMS AND METHODS," filed on Dec. 29, 2009, which published on Jul. 1, 2010 as U.S. Patent Application Publication No. US-2010-0168586-A1, each of which is incorporated by reference herein in its entirety.

STATEMENT REGARDING FEDERALLY SPONSORED RESEARCH OR DEVELOPMENT

This invention was made with government support under award numbers R21NS053684, R01 NS063226, and U54CA126513 from the National Institute of Health (NIH). The government has certain rights in this invention.

In particular, this invention was made with support for principal investigator Dr. Elizabeth Marjorie Clare Hillman from the Human Frontier Science Program, the National Institutes of Health (award number R01 NS063226), and the Wallace H. Coulter Foundation, and with support for principal investigator Matthew Bryan Bouchard from the National Defense Science and Engineering Graduate Fellowship of the Department of Defense. The government has certain rights in this invention.

BACKGROUND

Selective Plane Illumination Microscopy (SPIM) and its variants Ultramicroscopy, Objective-Coupled Planar Illumination Microscopy (OCPI), and Oblique Plane Microscopy (OPM) are approaches that can use light sheet imaging to image fluorescence contrast. Such approaches can provide diffraction or near diffraction limited resolution across 3D volumes. However, it is believed that these approaches require rigid alignment between the light sheet used for illumination and the camera used for detection. This makes it necessary to either translate the entire imaging system or the sample relative to the light sheet for 3D imaging.

Another approach, Optical Projection Tomography (OPT) can provide volumetric imaging based upon projection imaging using light. In this approach, light is shone directly through the sample and detected collinearly, in an analogous imaging technique to x-ray Computed Tomography (CT). The sample, or the complete imaging system must be physically rotated using a precision rotation stage to acquire projection images. A modified back-projection algorithm is then used to generate 3D images of absorbing or fluorescent contrast.

The present inventors have recognized that one problem with OPT and SPIM-type imaging approaches is that such techniques are limited to minimally or non-scattering samples or to larger ex-vivo, chemically cleared tissue samples. Additionally, the need for precise sample translation and/or rotation for OPT and SPIM significantly limits the rate at which these techniques can scan 3D volumes and the types of samples that can be imaged.

Laminar Optical Tomography (LOT) is an optical imaging approach that takes advantage of photon scattering in tissues by detecting backscattered light which has travelled to different depths within a sample. LOT can provide non-contact, scanning spot imaging to depths of up to 2 mm in living tissues and has recently been extended to allow simultaneous multispectral imaging of both absorption and fluorescence contrast. An example of LOT is described in Hillman et al. U.S. patent application Ser. No. 12/655,325, entitled OPTICAL IMAGING OR SPECTROSCOPY SYSTEMS AND METHODS," filed on Dec. 29, 2009, which published on Jul. 1, 2010 as U.S. Patent Application Publication No. US-2010-0168586-A1, each of which is incorporated by reference herein in its entirety. However, owing to its illumination and detection geometry, such LOT techniques are primarily useful to image scattering samples, as it is particularly configured to detect photons which have backscattered from the tissue.

OVERVIEW

This document describes, among other things, an imaging approach that can be referred to herein as Laser-Scanning Intersecting Plane Tomography (L-SIPT), which can provide a non-contact imaging geometry that can allow high speed volumetric scanning, such as of non-scattering to minimally scattering tissues. L-SIPT can make use of a single lens confocal theta microscope-type geometry and LOT-like off-axis detection geometry. An initial purpose of this technique can be to bridge the gap left by the LOT and OPT/SPIM imaging techniques to allow high-speed volumetric imaging of non-scattering to minimally scattering samples, for example in vivo tissues. In an example that can be based upon a single lens confocal theta microscope geometry and LOT off-axis detection geometry, the scanned region swept by our L-SIPT imaging approach can be scaled from micro-to macro-scales, such as through the choice of an appropriate set of lenses.

Additional purposes of the technique can include industrial sensing of subsurface flows, turbulence, or mixing dynamics, or other situations where high-speed 2D or 3D imaging of non-scattering or minimally scattering substances would be of value. The L-SIPT imaging geometry can allow it to detect both absorption and fluorescence contrast in scattering tissues, and fluorescence or other incoherent contrast in non-scattering samples. To detect fluorescence contrast, appropriate choice of illumination wavelength and optical emission filters can be selected based upon the specific sample being imaged with L-SIPT.

This section is intended, to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

This document describes, among other things, an imaging approach that can be referred to herein as Laser-Scanning Intersecting Plane Tomography (L-SIPT), which can provide a non-contact imaging geometry that can allow high speed volumetric scanning, such as of non-scattering to minimally scattering tissues.

Figure 1:
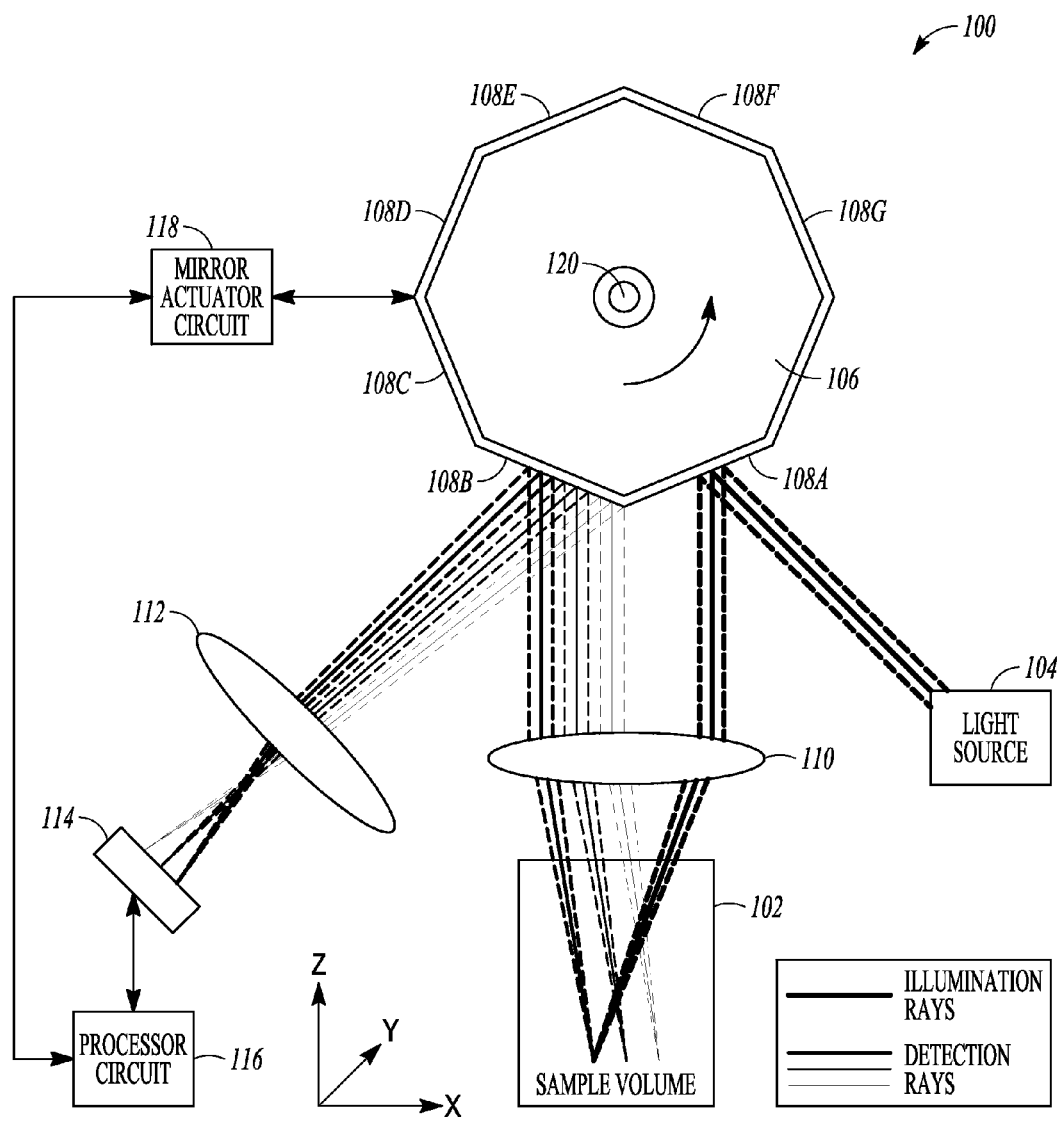
FIG. 1 is an example of a schematic illustration of an example of portions of an L-SIPT system and portions of an environment with which it can be used, such as with a sample volume, with ray tracings illustrative of an example of operating the system.

FIG. 1 is an example of a schematic illustration of an example of portions of an L-SIPT system 100 and portions of an environment with which it can be used, such as with a sample volume 102, with ray tracings illustrative of an example of operating the system 100. In this example, a light source 104 can include a collimated light source. Any collimated light source can be used in the various examples of the L-SIPT system 100 described herein. These can include a collimated laser beam (e.g., continuous-wave or time-varying), a collimated output of a supercontinuum laser, a collimated output of any narrow or broadband light source (e.g., a halogen lamp), or a collimated light emitting diode (LED) source. Other examples can include a fiber-coupled LED or other light source 104, such as for providing a single-frequency or multispectral, collimated beam or light sheet input for the system 100.

In an example, the collimated light can be provided to a planar or other reflector (or other light redirector) 108A that is in a fixed or other specified spatial relationship to a different planar or other reflector (or other light redirector) 108B. In an example, the reflectors 108A-B can include adjacent reflective surface facets of a rotating polygon, mirror 106. The rotating polygon mirror 106 can include other facets, such as to provide light redirectors, such as reflectors 108C-108G, as shown in the example of FIG. 1. By rotating the mirror 106, such as in the direction of the arrow shown in FIG. 1, a scan of the sample volume 102 can be provided. A scan lens 110 can be located in a path of the light that is provided by the light source 104 and reflectively redirected by the reflector 108A (or other facet then occupying such location as shown in FIG. 1). The scan lens 110 can be located in the incident light path between the reflector 108A and the sample volume 102. The scan lens 110 can refract such light, such as toward desired locations in the sample volume 102, such as indicated by the illustrative ray tracings shown in FIG. 1.

Light received (e.g., scattered light, fluorescence, etc.) from the different depths in the sample volume 102 can be refracted by the same scan lens 110 (or a different lens), such as toward desired locations on a second reflector 108B (or other light redirector).

Light reflectively redirected by the reflector 108B can be directed toward a lens 112, which, in turn, can refract such light toward a light detector 114. Light from different axial positions with respect to the scan lens 110 (corresponding to different depths within the sample) map via the scan lens 110, the reflector 108B and lens 112 to different lateral positions in the detector plane 114.

In an example, the light detector 114 can include a light detector array (for example, a linear CCD or other 1D or 2D detection array) that can be capable of detecting distinct individual measurements of light at different lateral locations along at least a first direction. In an example, the light detector 114 can include a single light detector that can be translated along at least a first direction such as to be capable of detecting distinct individual measurements of light at different locations along the first direction. In an example, the light detector 114 can include an at least 2D light detector array that can be capable of detecting distinct individual measurements of light at different locations along at least a first direction and also capable of detecting distinct individual measurements of light at different locations along a second direction that is orthogonal to the first direction, such as for a 3D volumetric imaging application. In an example, the light detector 114 can include a light detector that can be translated along at least a first direction such as to be capable of detecting distinct individual measurements of light at different locations along the first direction and that can also be translated along a second direction that is orthogonal to the first direction such as to be capable of detecting distinct individual measurements of light at different locations along the second direction, such as for a 3D volumetric imaging application. In an example, the light detector 114 can include a 1D or 2D fiber optic bundle that can be arranged to allow light from different lateral positions to be routed to multiple individual detectors, or a single detector such as via a fiber switch. The refraction of such light provided by the lens 112 can help focus such light such as to span a desired amount of the first direction of the light detector 114, a desired amount of the orthogonal second direction of the light detector 114, or both.

The example shown in FIG. 1 can use a high-speed polygon mirror 106 as a scanner to scan the input collimated beam or sheet of light through the sample volume 102 via reflector 108A and to de-scan the light returning from the sample via reflector 108B and direct it to the stationary detector 114. The reflectors 108A-B need not be implemented using the rotating polygon mirror 106 in any of the examples described herein. In any of the examples described herein, the scanner element of the L-SIPT system 100 can include one or more other techniques for redirecting light, such as one or more of a galvanometer, an actuated prism, a Digital Micromirror Device (DMD), another microelectromechanical system (MEMS) technology, an acousto-optic deflector (AOD), or Spatial Light Modulator (SLM). Technologies such as MEMS, DMD, or SLM devices can be capable of serving as light directors that can be controlled to provide the specified spatial relationship of the first light redirector to the second light redirector during the scan. Further, technologies such as MEMS, DMD, or SLM devices can be used to generate illumination patterns such as light sheets or Bessel beams as well as novel scan patterns (such as circles, ellipses, or random-access scan patterns). Such technologies can also allow miniaturization, such as to implement L-SIPT for endoscopic imaging applications. Appropriate adjustment of lens configuration can be provided, for example separate (or no) scan lenses can be used for incident and returning light from the sample.

A processor circuit 116 can be coupled to the light detector 114, such as to receive information about the light detected during a scan of the sample volume 102, which in an example can be obtained by rotating the scanning minor 106 such that light from different locations of the sample volume 102 can be acquired. In an example, the processor circuit 116 can store such information, such as in an on-board or auxiliary memory circuit, can perform signal-processing on such information (such as to reconstruct a 2D or 3D image of portions of the sample volume 102), or can store such image information or information derived therefrom, In an example, the processor circuit 116 can also provide one or more control signals, such as to one or more components of the system 100, such as for controlling operation. In an example, the processor circuit 116 can provide one or more control signals to a minor actuator circuit 118, which can control rotation of the minor 106. In an example, the mirror actuator circuit 118 can also provide minor position (e.g., scan angle) or motion information back to the processor circuit 116. Such scan angle or other feedback information can be used to control the minor 106. Such scan angle or other feedback information can be used to interpret the information from the light detector 114, e.g., being received at such corresponding scan angle of the mirror 106. In an example, the processor circuit 116 can provide information to one or more other components of the system 100, such as to the light detector 114, the light source 104, or the like, such as to control operation of such other components of the system 100 such as a sample translator.

In an example, the processor circuit 116 can be configured to include or access a processor-readable medium that can include instructions (e.g., code) or information (e.g., a look-up table or a model), such as to configure the processor circuit 116 to be capable of predicting, modeling, deriving, or translating (1) scan data provided by reflected or otherwise redirected light detected by the light detector 114 to (2) two-dimensional (2D) or three-dimensional (3D) image data at appropriate image pixel positions corresponding to locations within the sample 102 from which the reflected or otherwise redirected light detected by, the light detector 114 is received. The translating can include using information about (1) a scan angle and (2) a system characteristic such as a lens characteristic of the first lens, such as explained below with respect to FIG. 2.

Figure 2:
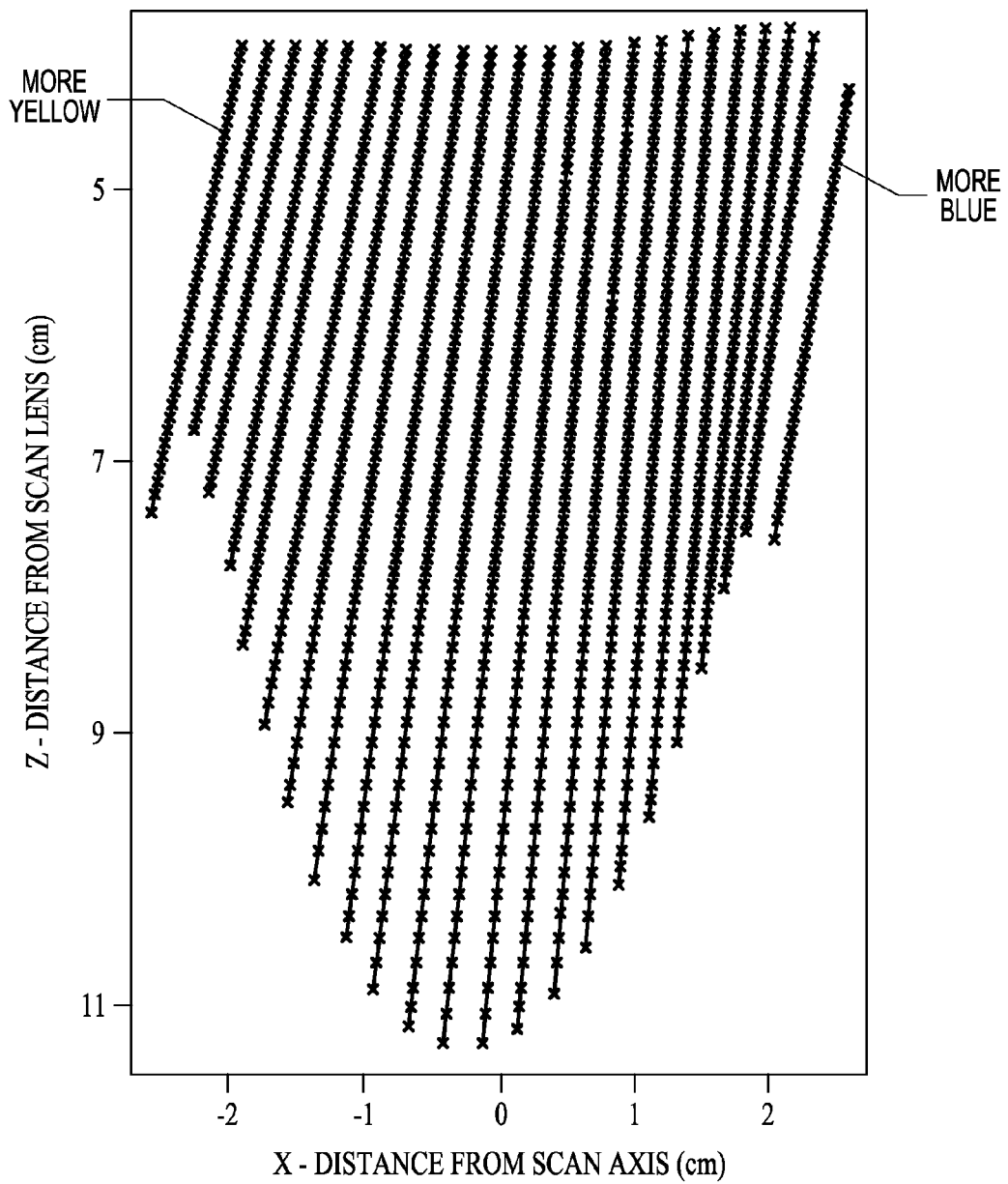
FIG. 2 is an illustrative example of a map of pixel positions of an image such as can be detected by a linear array light detector during scanning by rotating a polygon mirror scanning element over a coarse single sweep of the polygon facets.

FIG. 2 is an illustrative example of a map of pixel positions of an image such as can be detected by a linear array light detector 114 during scanning by rotating a polygon mirror 106 scanning element over a coarse single sweep of the polygon facets 108A-B. As the angle of the polygon mirror 106 changes, the positions mapped onto the detector elements of the linear array light detector 114 are shown in FIG. 2 to move from yellow to blue, with each detector element's lateral position represented by a dot in sequence along each of the lines in FIG. 2. The mapping shown in FIG. 2 is significantly down-sampled with respect to actual measurements, for illustrative clarity. In the example of FIG. 2, the x-axis represents distance (cm) from a scan lens axis (e.g., from left to right as drawn in FIG. 1), and the other axis is a z-axis that represents distance (cm) from the scan lens 110 or depth in the sample volume 102 (e.g. from top to bottom as drawn in FIG. 1). Thus, the x-z plane shown in FIG. 2 extends vertically into the sample volume in a direction that is parallel to the scan lens axis and to the illustrated plane of the rotating polygon mirror 106, as shown in the directional x-y-z legend of FIG. 1.

In an example, the processor circuit 116 can include or receive a model that represents a mapping between the physical scan positions and the measured data, such as the x-z representation shown in FIG. 2. Such mapping of the measured data can include using associated information about the scan angle at which such measured data was obtained, along with information about characteristics of the particular configuration of the system 100, such as a characteristic of the scan lens 110 (e.g., focal length, diameter, refractive index, etc.), distance between the scan lens 110 and the sample 110 or the reflectors 108A-B, a characteristic of the lens 112 (e.g., focal length, diameter, refractive index, etc.), distance between the lens 112 and the light detector 114 or the reflectors 108A-B. The mapping can also include or derive information about the sample, such as its surface geometry, refractive index, other optical properties (known or estimated) such as scattering, anisotropy, absorption, fluorescence, or the refractive index and geometry of any intermediate material or medium such as sample holders or matching fluid.

In an example, to understand the data generated by the L-SIPT system 100 and to convert this data from L-SIPT scanning measurement space to image space, custom raytracing software in MATLAB was developed. This raytracing software can be based around a graphical user interface (GUI) that allows the user to modify all system design properties. Raytracing can be performed with knowledge of the system characteristics, such as the positioning of all optical surfaces in the model—such as including the size and shape of lens surfaces and lens index of refraction. The refraction angles of each ray at each lens surface can be calculated using Snell's Law. The resulting forward model coordinate transform can allow mapping of the acquired data, which is in L-SIPT measurement space (e.g., specified by a scan angle of a polygon mirror 106 and specified system characteristics, e.g., detector-separation) to a Cartesian coordinate system, such as shown in the x-z image representation of FIG. 2.

The representation in FIG, 2 was generated by simulating the intersecting locations of the illumination beam with light traveling in directions such that it images onto each detector element, at a series of scan angles within a single facet sweep of the mirror 106. A first L-SIPT prototype was designed to image objects over a field of view spanning several centimeters. However, using the raytracing model, the system's lenses can readily be re-designed to provide much higher resolution imaging in non-scattering samples over smaller fields of view, such as approaching microscopy scales. Further, by incorporating Monte Carlo modeling of scattering into this forward model, the L-SIPT data can be suitable for LOT-style 3D image reconstruction in scattering tissues.

In an example, the system 100 in FIG. 1 can be used to image 3D samples using a 1D linear array light detector 114, such as where the object being imaged can be physically translated in a y-direction orthogonal to the x-z plane (or if the complete imaging system is translated relative to the sample).

The, processor circuit 116 can then use information regarding the y-position of each x-z plane scan to assemble a 3D image of the sample.

Figure 3:
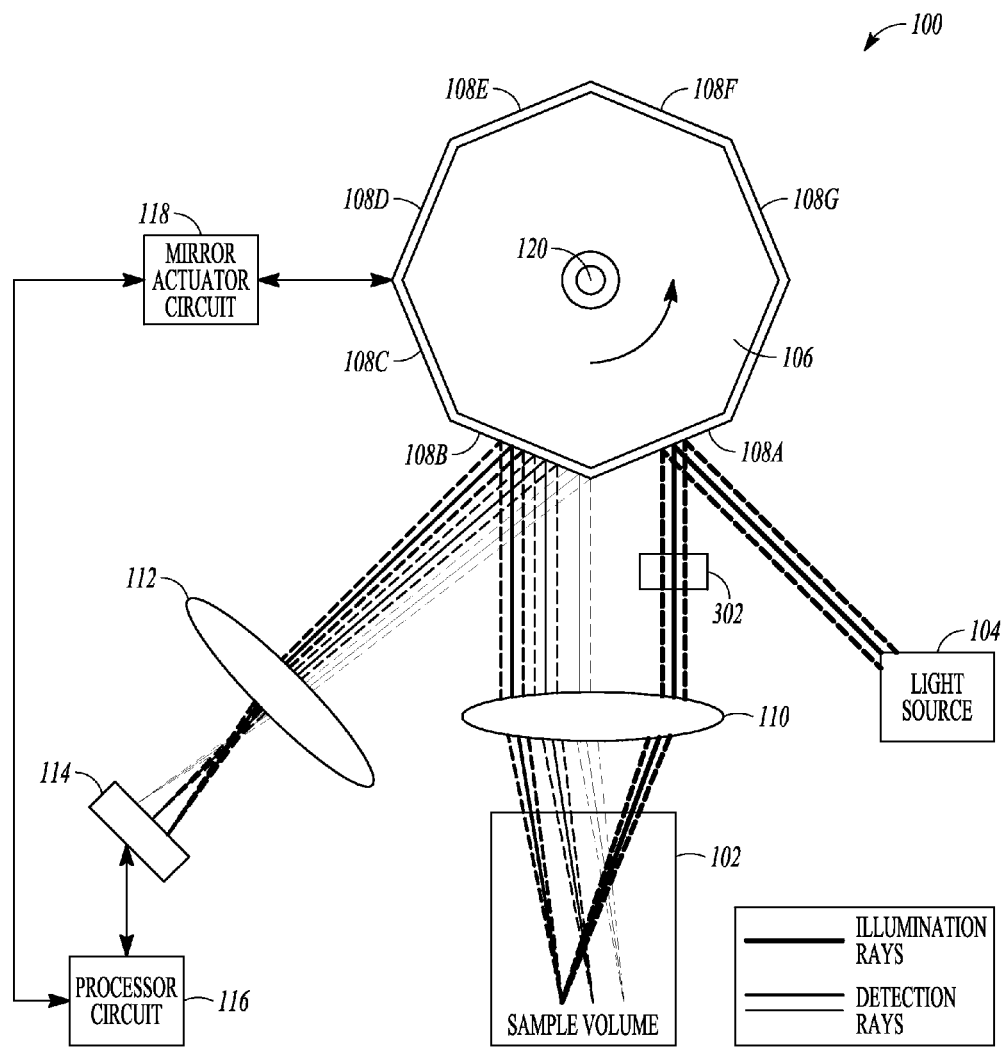
FIG. 3 is an example of a schematic illustration of an example of portions of an L-SIPT system and portions of an environment with which it can be used

FIG. 3 is an example of a schematic illustration of an example of portions of an L-SIPT system 100 and portions of an environment with which it can be used. FIG. 3 is similar, in certain respects, to FIG. 1. In the example of FIG. 3, the light detector 114 is capable of collecting 2D information, such as for generating a volumetric 3D image of the sample volume 102. In an example, the light detector 114 can include a 2D array that is capable of detecting individual measurements of light at different locations along a first direction, and that is also capable of detecting individual measurements of light at different locations along a second direction that is orthogonal to the first direction. In an example, the light detector can include at least one element that can be translated along the first direction to detect individual measurements of light at different locations along the first direction, and at least one (same or different) element that can be translated along the second direction to detect individual measurements of light at different locations along the second direction.

The example of FIG. 3 can include a cylindrical lens 302 in the incident light path, such as between the reflector 108A and the scan lens 110, or such as between the light source 104 and the reflector 108A, such as described in an article by Dwyer et al. entitled CONFOCAL REFLECTANCE THETA LINE SCANNING MICROSCOPE FOR IMAGING HUMAN SKIN IN VIVO, Optics Letters, Vol. 37, Issue 7, pp. 942-944 (2006), which is incorporated herein by reference in its entirety, including its description of line scanning. The cylindrical lens 302 can be configured to convert a collimated light beam (e.g., having a point-like circular cross-section looking into or away from a direction of the incident light) into a collimated light sheet (e.g., having an approximately linear cross-section looking into or away from a direction of the incident light). This can allow volumetric 3D imaging of the sample 102, such as by concurrently producing during the scanning (e.g., by rotating the mirror 106 over a single sweep of the polygon facets 108A-B) a series of x-z image slices such as shown in FIG. 2 for a range of positions in the y-direction direction simultaneously, corresponding to the additional rows of the 2D array light detector 114 Such volumetric 3D imaging can advantageously provide a high throughput and need not involve any translation or other movement of the sample volume 102 or contact with the sample volume 102.

The cylindrical lens 302 can be replaced by another optical element that can be selected from a range of other optical elements that are capable of generating a pre-defined illumination pattern or light sheet. Although the collimated light sheet has been described above as having an approximately linear cross-sectional profile, the present inventors have recognized that a refractive cylindrical lens 302 actually creates a light sheet that can more accurately be described as having an approximately hyperbolic profile. That is, the resulting light sheet becomes thinnest at the focal plane of the refractive cylindrical lens 302 and becomes larger away from such focal plane as the focused light diverges. Such non-ideality of a light sheet of varying thickness can be avoided by using a Bessel beam. Bessel beams are non-divergent, non-diffractive beams of light that can maintain their thickness over relatively long propagation distances. With respect to a L-SIPT system 100, a Bessel beam can be used to create a light sheet with a constant thickness, which can be scanned through the sample 102, such as to provide 3D volumetric imaging. This can improve the lateral resolution of the system (in the x-plane) when moving away from the focal plane of the scan lens 110. In an example, a SLM can be used, such as in the place of the cylindrical lens 302, such as to provide a Bessel beam or, if desired, a light sheet or other illumination pattern. In an example, the SLM can be placed between the light source 104 and the reflector 108. An example of using a Bessel beam is provided in an article by Fahrbach et al. entitled MICROSCOPY WITH SELF-RECONSTRUCTING BEAMS, Nature Photonics 4, 780-785 (2010), which is hereby incorporated by reference herein in its entirety, including its description of use of Bessel beams.

Figure 4:
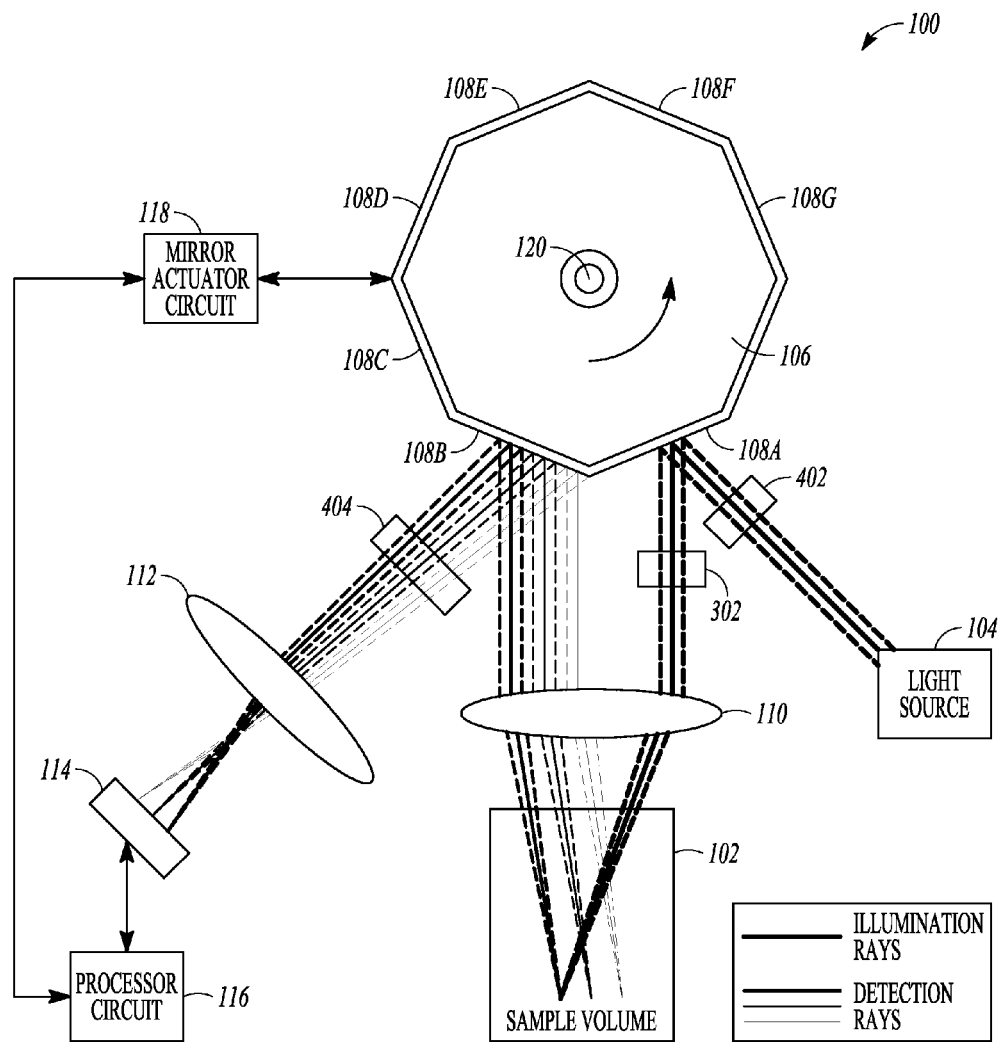
FIG. 4 is an example of a schematic illustration of an example of portions of an L-SIPT system and portions of an environment with which it can be used.

FIG. 4 is an example of a schematic illustration of an example of portions of an L-SIPT system 100 and portions of an environment with which it can be used. FIG. 4 is similar, in certain respects, to FIGS. 1 and 3. In an example, the light detector 114 can be capable of collecting 2D information, such as for generating a volumetric 3D image of the sample volume 102, such as described above. A cylindrical lens 302 or SLM can be provided, such as to provide a suitable incident light profile for such volumetric 3D imaging. In the example of FIG. 4, a fluorescence response from the sample 102 can be detected, and a resulting 2D area image or 3D volumetric image can be formed. This can include optionally providing a fluorescence excitation filter 402 in the path of the incident light, such as between the light source 104 and the reflector 108A, or between the reflector 108A and the scan lens 110, The fluorescence excitation filter 402 can adjust the incident light wavelengths to a desired value for exciting a fluorescence response from the sample volume 102 (e.g., where a broadband light source 104 is used). A fluorescence emission filter 404 can optionally be provided in the path of the light emitted from the sample volume, such as between the lens 112 and the reflector 108B or between the reflector 108B and the lens 110. The fluorescence emission filter 404 can separate the fluorescence response light wavelengths from light scattered from the sample 102 at the incident light wavelengths. The fluorescence excitation filter 402 or the fluorescence emission filter 404 can also optionally be similarly included in the configuration of the system 100 as shown in FIG. 1, or with other examples described herein.

Figure 5:
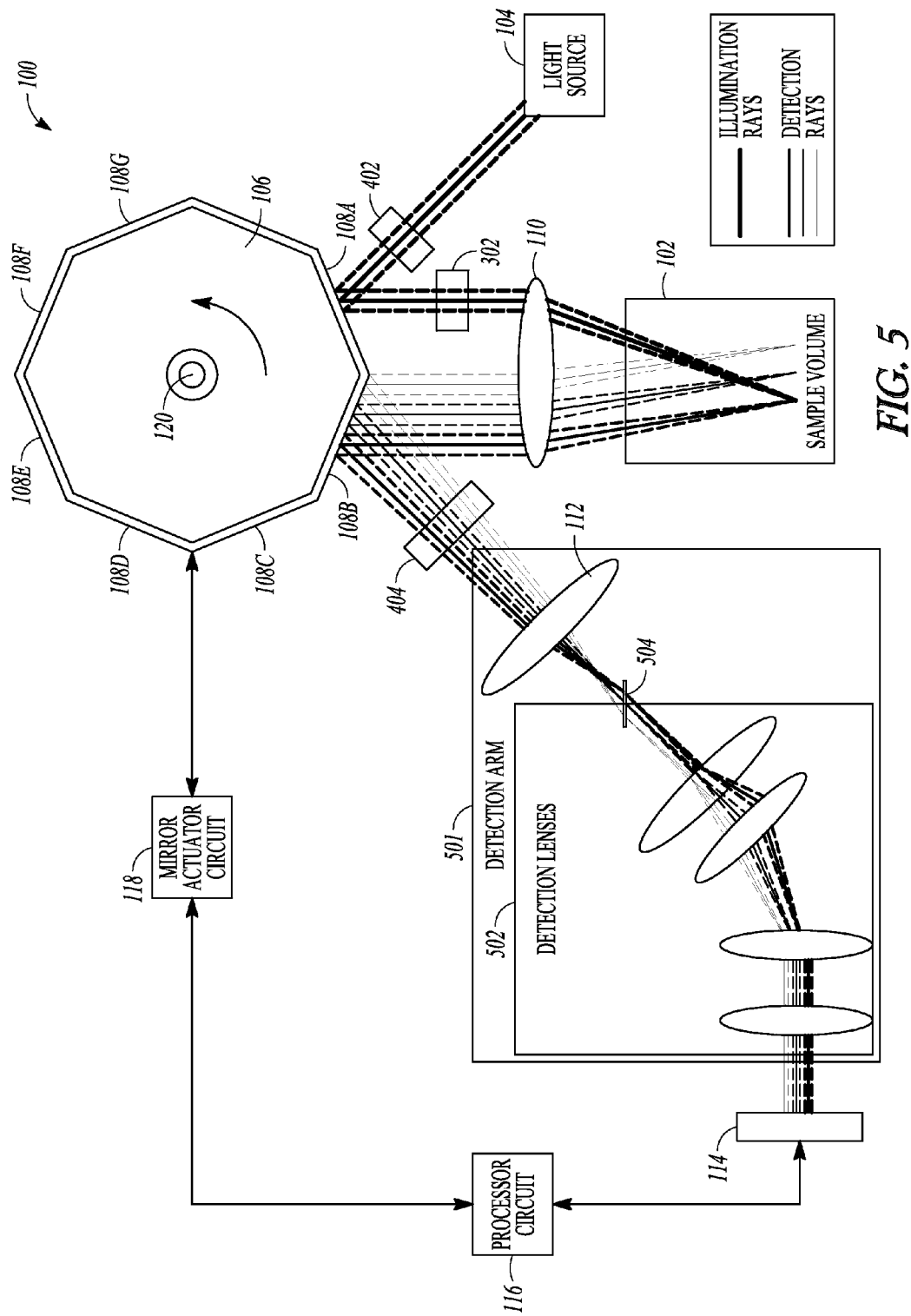
FIG. 5 is an example of a schematic illustration of an example of portions of an L-SIPT system and portions of an environment with which it can be used.
Figure 5:
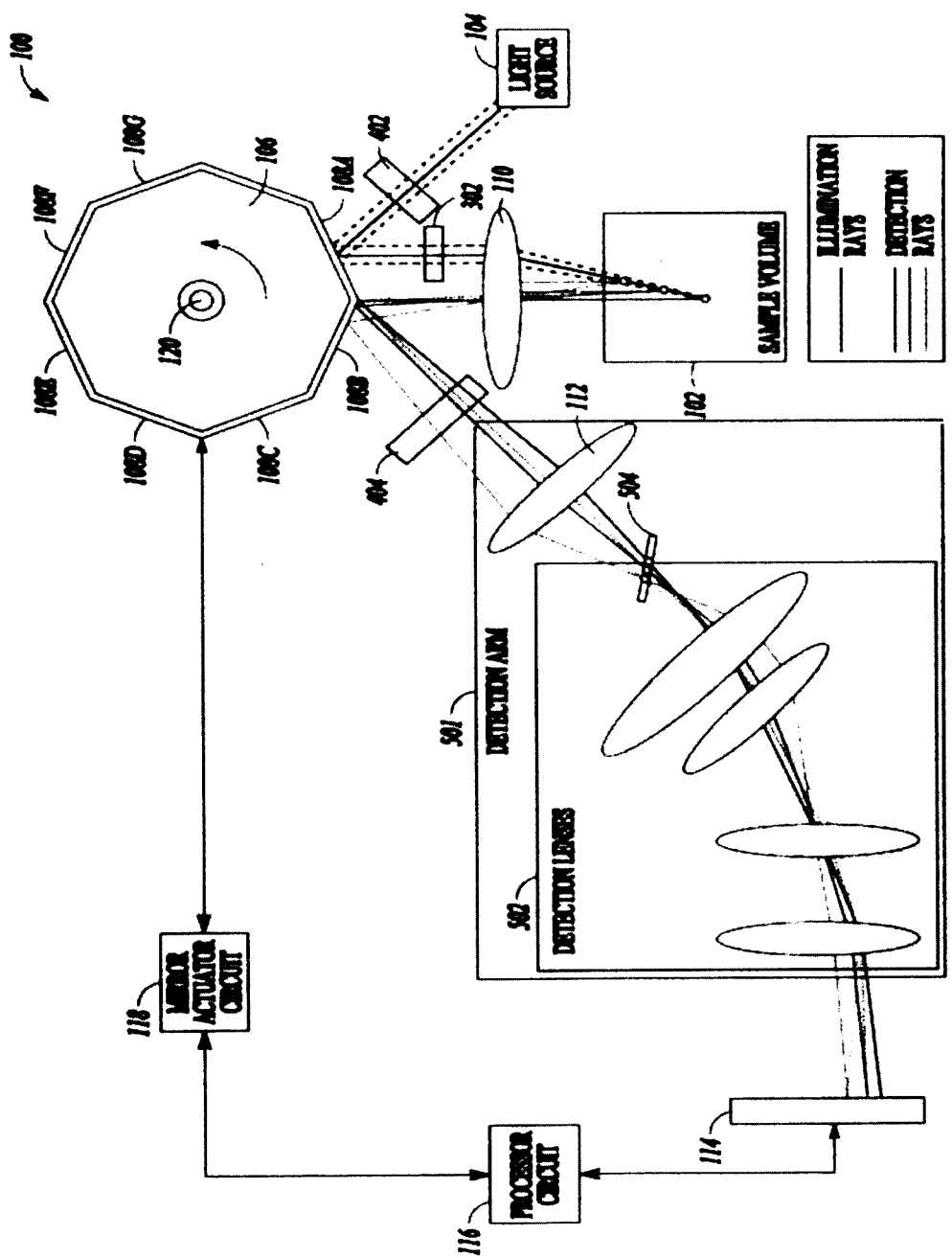

FIG. 5 is an example of a schematic illustration of an example of portions of an L-SIPT system 100 and portions of an environment with which it can be used. FIG. 5 is similar, in certain respects, to FIGS. 1 and 3-4, but illustrates an angle-correction configuration that can be used in any of the examples described herein, including those described with respect to FIGS. 1 and 3-5. The present inventors have recognized that, for a given illumination beam position, the rays of light emitted from the sample 102 will form an image (e.g., at an intermediate image plane 504) that is not orthogonal to the axis of the first detection lens 112 such that a detector 114 positioned as shown in FIG. 1 will generate images where deeper and shallower features of the object being imaged are out of focus with respect to an intermediate region that is in focus. However, the present inventors have also recognized that such defocusing can be compensated or substantially completely corrected, such as by using a defocus compensator lens arrangement 502 configured to receive light from different depths of the sample, and to compensate for a defocus associated with the angle of the image formed at intermediate image plane 504 after the first detector lens 112. Compensation for this angle could also be achieved using an SLM or other lens arrangement or a detector positioned or otherwise optimized to image while positioned at an angle corresponding to the original angle of the intermediate image plane. Techniques useful for understanding such defocusing, and compensation for such defocusing, are described in an article by C. Dunsby entitled OPTICALLY SECTIONED IMAGING BY OBLIQUE PLANE MICROSCOPY, Optics Express, Vol. 16, No. 25, December 2008, pages 20306-20316, which is hereby incorporated by reference herein in its entirety, including its description of techniques useful for understanding such defocusing, and compensation for such defocusing, such as for use by the defocus compensator lens arrangement 502.

Thus, FIG. 5 illustrates an example of an angle-corrected L-SIPT system 100 that can correctly align the focal plane of the light detector 114 with the intermediate image at intermediate image plane 504 of the scanned illumination beam provided by the light source 104 to the sample 102. This configuration can provide increased spatial resolution as opposed to a non-angle corrected L-SIPT system 100 that does not include defocus decompensation. The detection aim 501, which can include the lens 112 and the defocus compensator lens arrangement 502 can build upon the Oblique Planar Microscopy detection geometry described and incorporated above. The cylindrical lens 302, which can be placed in the incident light path before or after the polygon scanner mirror 106 and before the scan lens 110 can be used to create a focused sheet of light (e.g., with the plane of the light sheet coming out of the paper). This sheet of light can be scanned through the sample 102, providing a 3D volume sweep of the scan for a single rotation of the polygon facet of the mirror 106. A 2D array light detector 114 can be used for this configuration. This example can perform 3D volume scans without needing to translate the sample 102 relative to the imaging system 100. As such, this system 100 can be used, for example, to image living samples in 3D at high speeds.

By contrast, if the defocus compensator lens arrangement 502 were not included to align the focal plane of the light detector 114 to the scanned incident light, the resolution and maximum field of view will be reduced. However, such an arrangement (e.g., such as shown in the example of FIG. 1) would provide relative simplicity of design that can still allow the detector pixels of the light detector 114 to image the plane illuminated by the incident light as it is scanned across the field of view of the system 100.

The region swept by the imaging system 100 can be scaled from micro-to macro-scales through the choice of an appropriate set of lenses, making the L-SIPT system 100 highly scalable, e.g., capable of imaging dynamic 3D systems on length scales including ranges from micrometers to centimeters. In non-scattering to moderately scattering tissues, the L-SIPT system can be configured to scan entire volumes in a single sweep by forming the collimated light input into a light sheet and by using a high-speed 2D detector array 114, as discussed above.

The time to perform a scan is directly related to the scan rate of the chosen scanning device. For example, an off-the-shelf polygon mirror can be used to scan up to 4,000 Hz. This can allow 3D imaging at 4000 scans per second, assuming a fast enough detector array 114 is also included in the system 100.

In an example, at microscopy length scales (e.g., single to tens of micrometers in length) the techniques of the L-SIPT system 100 can be combined with a number of other microscopy techniques to create corresponding new high speed microscopy techniques.

In an example, Fluorescence Lifetime Imaging Microscopy (FLIM) can use a light source with a time-varying intensity, and a detector capable of measuring the time taken for light to reach it with respect to the timing of the incident light to detect contrast provided by the differences in fluorescence decay rates of fluorophores. L-SIPT can be similarly implemented to detect FLIM contrast by using an appropriate source and detector. FLIM can be used, for example, for identifying individual molecules or detecting changes in the environment of a fluorophore such that the environment (e.g., pH, viscosity, temperature, or the presence of another fluorophore) alters the fluorophore's fluorescent lifetime. A description of FLIM is available in an article entitled APPLICATIONS IN CONFOCAL MICROSCOPY: FLUORESCENCE LIFETIME IMAGING MICROSCOPY (FLIM), available at <http://www.olympusfluoview.com/applications/filmintro.html (visited on Dec. 2, 2010)>, which is hereby incorporated by reference herein in its entirety, including its description of FLIM.

In an example, instrumentation similar to that used for FLIM can also be adapted to make "time-resolved" measurements of for example absorption, scattering or fluorescence contrast, in minimally scattering tissue. In an example, the temporal delays of detected photons can be used to improve image reconstructions generated using the L-SIPT system 100. For example, photons that undergo a single scattering event in a tissue or other sample 102 will arrive at the light detector 114 sooner than photons that travel more tortuous paths through the tissue or other sample 102. The photon arrival time, combined with knowledge of the specified spatial distances between the sample 102 and the temporally resolved light detector 114 can provide information that can confine the origin of the photon to a specific region of space, thus improving the spatial resolution of images acquired of minimally scattering tissues or other samples 102.

In an example, Förster Resonance Energy Transfer (FRET) can allow precise measurement of the distances between pairs of fluorescence molecules. The L-SIPT system 100 described herein can be used to perform FRET techniques without requiring any additional hardware. FRET techniques can involve knowledge of how a specific pair of fluorophores interact with each other. In FRET techniques, the two molecules in question are related by their excitation and emission spectra: the donor molecule has an emission spectrum that overlaps with the excitation spectrum of the acceptor molecule. When this is the case, and the donor and acceptor molecules are in very close proximity to each other (e.g., on the order of 1-10 nanometers), excitation of the donor molecule will result in the detectable emission of the acceptor light as well as changes in the fluorescence lifetime of the donor. By imaging using the L-SIPT system 100, or an extended FLIM-capable version of L-SIPT, it is possible to use FRET techniques to discern when the donor and acceptor are in very close proximity to each other. FRET can be used in protein binding experiments. A description of FRET is provided in an article entitled APPLICATIONS IN CONFOCAL MICROSCOPY: FLUORESCENCE RESONANCE ENERGY TRANSFER (FRET) MICROSCOPY, available at <http://olympusfluoview.com/applications/fretintro.html (visited on Dec. 2, 2010)>, which is hereby incorporated by reference herein in its entirety, including its description of FRET techniques.

In an example, multispectral illumination techniques can be used in the L-SIPT system 100, such as by using multiple, co-aligned, collimated light sources (e.g., lasers at different wavelengths), supercontinuum or broadband light sources. Multispectral illumination can be applied to virtually all microscopy techniques by providing a wavelength-dependent source of contrast. In an example, the L-SIPT system 100 can implement multispectral detection. In an example, the light detector 114 can include color cameras, e.g., multiple cameras that can be separated by spectrally discriminating optical elements, such as dichroic beamsplitters, using a dispersive element (e.g., prism or grating) to separate out the spectral elements of the returning light from the sample 102 onto a 2D array or onto multiple arrays. Imaging spectrometry can be introduced using a Liquid Crystal Tunable Filter (LCTF).

In an example, Stimulated Emission Depletion Microscopy (STED) can provide a "super-resolution" microscopy technique that can provide spatial resolution beyond the diffraction limit. STED can be performed by illuminating a fluorescence sample with a diffraction-limited beam as in confocal microscopy. Overlaid on edges of the excitation beam can be an emission depletion beam that can cause the fluorophore to non-radiatively decay. In this way, the emitted fluorescent light can be constrained to come from a specific spatial location that can be made arbitrarily small and below the conventional diffraction limit of optical microscopy. In an example, the L-SIPT system 100 can be used to perform STED by encasing the illumination beam or light sheet from the light source 104 within "emission depletion" shaped beams or light sheets to increase L-SIPT's lateral resolution. A description of STED techniques is described in an article by Dyba et al. entitled STED-MICROSCOPY . . . OVERCOMES THE DIFFRACTION LIMIT IN A FUNDAMENTAL WAY, http://www.mpibpc.mpg.de/groups/hell/STED.htm (visited Dec. 3, 2010), which is hereby incorporated herein by reference in its entirety, including its description of STED techniques.

OTHER EXAMPLES

The systems and methods described herein can address the problem of high-speed volumetric optical imaging. While existing methods can allow optically clear, dead samples of tissue to be imaged at slow speeds, the techniques described herein can allow high-speed imaging in both cleared and scattering tissues. The present techniques can be applied to imaging of biomedical samples for research, and potentially for diverse areas such as industrial fluid mixing, 3D recording of convection in gasses and liquids, bubble formation etc. Examples of commercial applications include industrial or environmental detection of subsurface flows/fluid mixing in tubes, convection and turbulent flow patterns etc. at high spatiotemporal resolution, etc.

In certain examples, the systems and methods described herein do not require translation of the sample relative to the imaging system to render 3-dimensional data. The systems and methods described herein can image in a non-contact geometry, at high speeds, but gain stereoscopic-type information from the sample without requiring multiple cameras or translating the sample. L-SIPT also has the capacity to image both cleared and scattering samples. Existing approaches are very limited in their applications to small, cleared, dead samples that need to be translated within the field of view.

Additional Notes & Examples

Example 1 can include subject matter that can include an imaging apparatus comprising: a first lens, located and configured to receive from a sample light received from different depths of the sample; a first light redirector, located and configured to receive via the first lens and to redirect light received from the different depths of the sample to provide redirected light to a light detector capable of detecting individual measurements of light at different locations along a first direction; and a second light redirector, located and configured to redirect light received from a light source to provide redirected light to the sample, wherein the second light redirector is in a specified spatial relationship to the first light redirector, and wherein the first and second light redirectors are configured to be adjusted during a scan of the sample so as to provide the specified spatial relationship during the scan.

In Example 2, the subject matter of Example 1 can optionally be configured such that the first lens is located and configured to refract light, from the light source and redirected by the second light redirector, to provide refracted light to the sample.

In Example 3, the subject matter of any one of Examples 1 or 2 can optionally include a second lens that is located and configured to refract the light, received from the different depths of the sample and redirected by the first light redirector, to provide refracted light to the light detector.

In Example 4, the subject matter of any one of Examples 1-3 can optionally include a mirror comprising a first facet for the first light redirector and a second facet for the second light redirector, wherein the mirror includes the first facet being affixed to the second facet to fix the specified spatial relationship of the first light redirector to the second light redirector during a scan in which the mirror is rotated to move the first and second light redirectors together.

In Example 5, the subject matter of any one of Examples 1-4 can optionally be configured such that the first and second light redirectors are capable of being controlled to provide the specified spatial relationship of the first light redirector to the second light redirector during the scan.

In Example 6, the subject matter of any one of Examples 1-5 can optionally further comprising the light source, and wherein the light source comprises a collimated light source configured to provide a light beam or light sheet.

In Example 7, the subject matter of any one of Examples 1-6 can optionally comprise a processor circuit configured to include or access a processor-readable medium that includes instructions or information that configure the processor circuit to be capable of translating (1) scan data provided by redirected light detected by the light detector to (2) two-dimensional (2D) or three-dimensional (3D) image data at appropriate image pixel positions corresponding to locations within the sample from which the redirected light detected by the light detector is received, the translating including using information about (1) a scan angle and (2) a lens characteristic of the first lens.

In Example 8, the subject matter of any one of Examples 1-7 can optionally further comprise the light detector, wherein the light detector comprises a one-dimensional (1D) light detector array.

In Example 9, the subject matter of any one of Examples 1-8 can optionally further comprise the light detector, wherein the light detector comprises a two-dimensional (2D) light detector array.

In Example 10, the subject matter of any one of Examples 1-9 can optionally comprise a cylindrical lens, configured to refract light received from the light source to provide a light sheet to the sample for 3D imaging.

In Example 11, the subject matter of any one of Examples 1-10 can optionally comprise a defocus compensator lens arrangement configured to receive light received from different depths of the sample, and to compensate for a defocus.

In Example 12, the subject matter of any one of Examples 1-11 can optionally comprise a fluorescence emission filter, located and configured to filter redirected light received from the different depths of the sample.

Example 13 can include, or can optionally be combined with the subject matter of any one of Examples 1-12 to include, an imaging apparatus comprising: a light source, including a collimated light source configured to provide a light beam or a light sheet; a light detector capable of detecting individual measurements of light at different locations along a first direction; a first lens, located and configured to receive from a sample light received from different depths of the sample; a first light redirector, comprising a first reflector, located and configured to receive via the first lens and to redirect light received from the different depths of the sample to provide redirected light to the light detector; a second lens, located and configured to refract the light received from the different depths of the sample and redirected by the first light redirector, to provide refracted light to the light detector; a second light redirector, comprising a second reflector, located and configured to redirect light received from the light source to provide redirected light to the sample via the first lens, wherein the second light redirector is in a specified fixed spatial relationship to the first light redirector, and wherein the first and second light redirectors are adjacent facets on a rotating polygon mirror and are configured to move together during a scan of the sample so as to provide the specified fixed spatial relationship during the scan of the sample; and a processor circuit configured to include or access a processor-readable medium that includes instructions or information that configure the processor circuit to be capable of translating (1) scan data provided by redirected light detected by the light detector to (2) two-dimensional (2D) or three-dimensional (3D) image data at appropriate image pixel positions corresponding to locations within the sample from which the redirected light detected by the light detector is received, the translating including using information about (1) a scan angle and (2) a lens characteristic of the first lens.

In Example 14, the subject matter of any one of Examples 1-13 can optionally be configured such that: the light detector comprises a two-dimensional (2D) light detector array; and the imaging apparatus comprises a cylindrical lens, configured to refract light received from the light source to provide a light sheet to the sample for 3D imaging.

Example 15 can include, or can be combined with the subject matter of any one of Examples 1-14 to optionally include, subject matter (such as a method, a means for performing acts, or a machine-readable medium including instructions that, when performed by the machine, cause the machine to perform acts) comprising: receiving, from a sample, light from different depths of the sample; redirecting, using a first light redirector, the light received from the sample to provide light to a light detector capable of detecting individual measurements of light at different locations along a first direction; redirecting light from a light source, using a second light redirector, to provide light to the sample, wherein the first and second light redirectors are configured in a specified spatial relationship to each other; and adjusting the first and second light redirectors during a scan of the sample so as to provide the specified spatial relationship during the scan.

In Example 16, the subject matter of any one of Examples 1-15 can optionally include moving the first and second light redirectors together to provide during the scan to provide the specified spatial relationship during the scan, In Example 17, the subject matter of any one of Examples 1-16 can optionally include refracting light from the sample to be provided to the first light redirector; refracting light from the light source to be provided to the sample; and sharing a refractive lens to refract light from the sample to be provided to the first light redirector and to refract light from the light source to be provided to the sample.

In Example 18, the subject matter of any one of Examples 1-17 can optionally include rotating a multifaceted mirror during the scan to provide the specified spatial relationship during the scan.

In Example 19, the subject matter of any one of Examples 1-18 can optionally include scanning the sample, including repeating light detection at different rotational positions of the mirror.

In Example 20, the subject matter of any one of Examples 1-19 can optionally include translating (1) scan data provided by redirected light detected by the light detector to (2) two-dimensional (2D) or three-dimensional (3D) image data at appropriate image pixel positions corresponding to locations within the sample from which the redirected light detected by the light detector is received, the translating including using information about (1) a scan angle and (2) a lens characteristic of a first lens.

In Example 21, the subject matter of any one of Examples 1-20 can optionally include compensating light, received from different depths of the sample, for a defocus.

Example 22 can include, or can optionally be combined with the subject matter of any one of Examples 1-21 to optionally include, subject matter (such as a method, a means for performing acts, or a machine-readable medium including instructions that, when performed by the machine, cause the machine to perform acts) comprising: receiving, from a sample, light received from different depths of the sample; redirecting, using a first light redirector, the light received from the sample to provide light to a light detector capable of detecting light at different locations along a first direction; refracting light from the sample to be provided to the first light redirector; redirecting light from a light source, using a second light redirector, to provide light to the sample, wherein the first and second light redirectors are positioned in a fixed spatial relationship to each other; refracting light from the light source to be provided to the sample by sharing a lens that is also used in the refracting light from the sample to be provided to the first light redirector; scanning the sample, the scanning including: rotating a multifaceted mirror in which adjacent facets provide the first and second light redirectors that rotate together so as to provide a specified fixed spatial relationship to each other during the scan; and repeating light detection at different rotational positions of the mirror; and translating (1) scan data provided by redirected light detected by the light detector to (2) two-dimensional (2D) or three-dimensional (3D) image data at appropriate image pixel positions corresponding to locations within the sample from which the redirected light detected by the light detector is received, the translating including using information about (1) a scan angle and (2) a lens characteristic of a first lens.

In Example 23, the subject matter of any one of Examples 1-22 can optionally include generating a 3D image reconstruction of the sample using a two-dimensional (2D) light detector array.

In Example 24, the subject matter of any one of Examples 1-23 can optionally include compensating light, received from different depths of the sample, for a defocus associated with an angle of incidence in the sample that is non-orthogonal to an angle of detection of the sample.

The above detailed description includes references to the accompanying drawings, which form a part of the detailed description. The drawings show, by way of illustration, specific embodiments in which the invention can be practiced, These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used, merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An imaging apparatus comprising:
   a first lens, located and configured to receive from a sample light received from different depths within the sample volume;
   a first light redirector, located and configured to receive via the first lens and to redirect light received from the different depths within the sample volume to provide redirected light to a light detector capable of detecting individual measurements of light at different locations along a first direction; and
   a second light redirector, located and configured to redirect light received from a light source to provide redirected light to the sample, wherein the second light redirector is in a specified spatial relationship to the first light redirector, and wherein the first and second light redirectors are configured to be adjusted during a scan of the sample so as to provide the specified spatial relationship during the scan.

2. The imaging apparatus of claim 1, wherein the first lens is located and configured to refract light, from the light source and redirected by the second light redirector, to provide refracted light to the sample.

3. The imaging apparatus of claim 2, including a second lens that is located and configured to refract the light, received from the different depths within the sample volume and redirected by the first light redirector, to provide refracted light to the light detector.

4. The imaging apparatus of claim 1, including a mirror comprising a first facet for the first light redirector and a second facet for the second light redirector, wherein the mirror includes the first facet being affixed to the second facet to fix the specified spatial relationship of the first light redirector to the second light redirector during a scan in which the mirror is rotated to move the first and second light redirectors together.

5. The imaging apparatus of claim 1, wherein the first and second light redirectors are capable of being controlled to provide the specified spatial relationship of the first light redirector to the second light redirector during the scan.

6. The imaging apparatus of claim 1, further comprising the light source, and wherein the light source comprises a collimated light source configured to provide a light beam or light sheet.

7. The imaging apparatus of claim 1, comprising a processor circuit configured to include or access a processor-readable medium that includes instructions or information that configure the processor circuit to be capable of translating (1) scan data provided by redirected light detected by the light detector to (2) two-dimensional (2D) or three-dimensional (3D) image data at appropriate image pixel positions corresponding to locations within the sample from which the redirected light detected by the light detector is received, the translating including using information about (1) a scan angle and (2) a lens characteristic of the first lens.

8. The imaging apparatus of claim 7, further comprising the light detector, and wherein the light detector comprises a one-dimensional (1D) light detector array.

9. The imaging apparatus of claim 7, further comprising the light detector, and wherein the light detector comprises a two-dimensional (2D) light detector array.

10. The imaging apparatus of claim 9, comprising a cylindrical lens, configured to refract light received from the light source to provide a light sheet to the sample for 3D imaging.

11. The imaging apparatus of claim 1, comprising a defocus compensator lens arrangement configured to receive light received from different depths within the sample volume, and to compensate for a defocus.

12. The imaging apparatus of claim 1, further comprising a fluorescence emission filter, located and configured to filter redirected light received from the different depths within the sample volume.

13. A method comprising:
receiving, from a sample, light from different depths within the sample volume;
redirecting, using a first light redirector, the light received from the sample to provide light to a light detector capable of detecting individual measurements of light at different locations along a first direction;
redirecting light from a light source, using a second light redirector, to provide light to the sample, wherein the first and second light redirectors are configured in a specified spatial relationship to each other; and
adjusting the first and second light redirectors during a scan of the sample so as to provide the specified spatial relationship during the scan.

14. The method of claim 13, comprising moving the first and second light redirectors together to provide during the scan to provide the specified spatial relationship during the scan.

15. The method of claim 13, comprising:
refracting light from the sample to be provided to the first light redirector;
refracting light from the light source to be provided to the sample; and
sharing a refractive lens to refract light from the sample to be provided to the first light redirector and to refract light from the light source to be provided to the sample.

16. The method of claim 13, comprising rotating a multifaceted mirror during the scan to provide the specified spatial relationship during the scan.

17. The method of claim 16, comprising scanning the sample, including repeating light detection at different rotational positions of the mirror.

18. The method of claim 13, comprising translating (1) scan data provided by redirected light detected by the light detector to (2) two-dimensional (2D) or three-dimensional (3D) image data at appropriate image pixel positions corresponding to locations within the sample from which the redirected light detected by the light detector is received, the translating including using information about (1) a scan angle and (2) a lens characteristic of a first lens.

19. The method of claim 13, comprising compensating light, received from different depths in within the sample volume, for a defocus.

20. An imaging apparatus comprising:
a light source, and wherein the light source comprises a collimated light source configured to provide a light beam or light sheet;
a light detector that comprises a two-dimensional (2D) light detector array;
a first lens, located and configured to receive from a sample light received from different depths within the sample volume;
a first light redirector, located and configured to receive via the first lens and to redirect light received from the different depths within the sample volume to provide redirected light to a light detector capable of detecting individual measurements of light at different locations along a first direction;
a second light redirector, located and configured to redirect light received from the light source to provide redirected light to the sample, wherein the second light redirector is in a specified spatial relationship to the first light redirector, and wherein the first and second light redirectors are configured to be adjusted during a scan of the sample so as to provide the specified spatial relationship during the scan, wherein the first lens is located and configured to refract light, from the light source and redirected by the second light redirector, to provide refracted light to the sample; and
a second lens that is located and configured to refract the light, received from the different depths within the sample volume and redirected by the first light redirector, to provide refracted light to the light detector;
a mirror comprising a first facet for the first light redirector and a second facet for the second light redirector, wherein the mirror includes the first facet being affixed to the second facet to fix the specified spatial relationship of the first light redirector to the second light redirector during a scan in which the mirror is rotated to move the first and second light redirectors together, wherein the first and second light redirectors are capable of being controlled to provide the specified spatial relationship of the first light redirector to the second light redirector during the scan;
a processor circuit configured to include or access a processor-readable medium that includes instructions or information that configure the processor circuit to be capable of translating (1) scan data provided by redirected light detected by the light detector to (2) two-dimensional (2D) or three-dimensional (3D) image data at appropriate image pixel positions corresponding to locations within the sample from which the redirected light detected by the light detector is received, the translating including using information about (1) a scan angle and (2) a lens characteristic of the first lens;
a cylindrical lens, configured to refract light received from the light source to provide a light sheet to the sample for 3D imaging;
a defocus compensator lens arrangement configured to receive light received from different depths of the sample, and to compensate for a defocus; and
a fluorescence emission filter, located and configured to filter redirected light received from the different depths of the sample.

21. A method comprising:
receiving, from a sample, light from different depths within the sample volume;
refracting light, with a shared refractive lens, from the sample to be provided to a first light redirector;
redirecting, using the first light redirector, the light received from the sample to provide light to a light detector capable of detecting individual measurements of light at different locations along a first direction;
refracting light, with the shared refractive lens, from a light source to be provided to the sample;
redirecting light from the light source, using a second light redirector, to provide light to the sample, wherein the first and second light redirectors are configured in a specified spatial relationship to each other;
moving the first and second light redirectors together by rotating a multifaceted mirror during a scan of the sample so as to provide the specified spatial relationship during the scan;
translating (1) scan data provided by redirected light detected by the light detector to (2) two-dimensional (2D) or three-dimensional (3D) image data at appropriate image pixel positions corresponding to locations within the sample from which the redirected light detected by the light detector is received, the translating including using information about (1) a scan angle and (2) a lens characteristic of a first lens;

compensating light, received from different depths of the sample, for a defocus; and scanning the sample, including repeating light detection at different rotational positions of the mirror.

22. An imaging apparatus comprising:

a first lens, located and configured to receive from a sample light received from different depths in the sample volume;

a first light redirector, located and configured to receive via the first lens and to redirect light received from the different depths within the sample volume to provide redirected light to a light detector capable of detecting individual measurements of light at different locations along a first direction;

a second light redirector, located and configured to redirect light received from a light source to provide redirected light to the sample, wherein the second light redirector is in a specified spatial relationship to the first light redirector, and wherein the first and second light redirectors are configured to be adjusted during a scan of the sample so as to provide the specified spatial relationship during the scan; and a processor circuit configured to include or access a processor-readable medium that includes instructions or information that configure the processor circuit to be capable of translating (1) scan data provided by redirected light detected by the light detector to (2) two-dimensional (2D) or three-dimensional (3D) image data at appropriate image pixel positions corresponding to locations within the sample from which the redirected light detected by the light detector is received.

23. An imaging apparatus comprising:

a first lens, located and configured to receive from a sample light received from different depths within the sample volume;

a first light redirector, located and configured to receive via the first lens and to redirect light received from the different depths within the sample volume to provide redirected light to a light detector capable of detecting individual measurements of light at different locations along a first direction; and a second light redirector, located and configured to redirect light received from a light source to provide redirected light to the sample, wherein the second light redirector is in a specified spatial relationship to the first light redirector, and wherein the first and second light redirectors are configured to be adjusted during a scan of the sample so as to provide the specified spatial relationship during the scan; and a processor circuit configured to provide an image of a region within the sample including an image of the different depths within the sample volume.

24. An imaging apparatus comprising:

a first lens, located and configured to receive from a sample light received from different depths within the sample volume;

a first light redirector, located and configured to receive via the first lens and to redirect light received from the different depths within the sample volume to provide redirected light to a light detector capable of detecting individual measurements of light at different locations along a first direction; and a second light redirector, located and configured to redirect light received from a light source to provide redirected light to the sample, wherein the second light redirector is in a specified spatial relationship to the first light redirector, and wherein the first and second light redirectors are configured to be adjusted during a scan of the sample so as to provide the specified spatial relationship during the scan, wherein the first lens and the first and second light redirectors are configured to cooperate to move a focal plane through the different depths within the sample volume during a scanning of the sample.

* * * * *

UNITED STATES PATENT AND TRADEMARK OFFICE
CERTIFICATE OF CORRECTION

Page 1 of 2

PATENT NO. : 8,619,237 B2
APPLICATION NO. : 12/961074
DATED : December 31, 2013
INVENTOR(S) : Hillman et al.

It is certified that error appears in the above-identified patent and that said Letters Patent is hereby corrected as shown below:

In the drawings,

Sheet 5 of 5, Fig. 5, delete

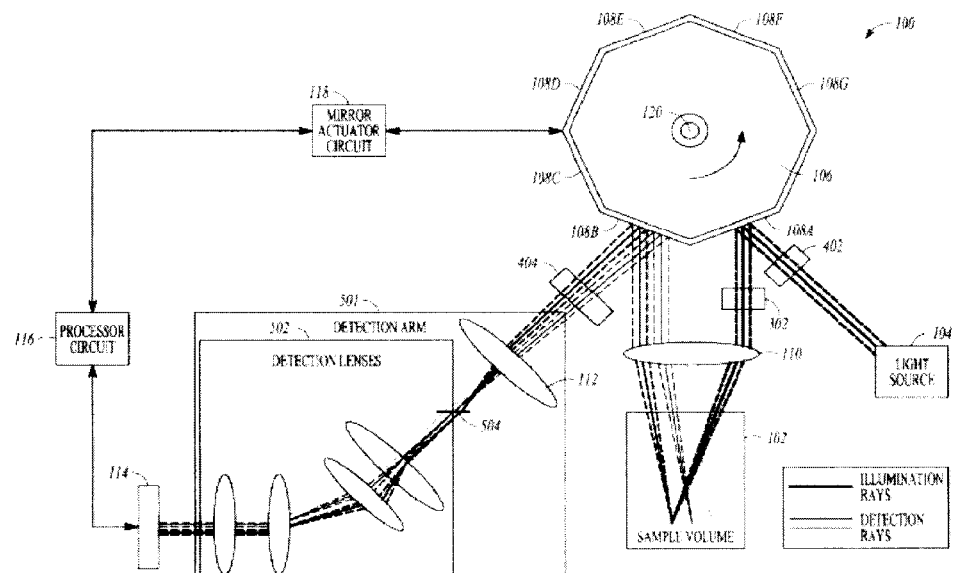

and insert as shown on attached sheet.

Signed and Sealed this
Sixth Day of October, 2015

Michelle K. Lee
*Director of the United States Patent and Trademark Office*